United States Patent [19] [11] 4,195,513
Cohen [45] Apr. 1, 1980

[54] METHODS OF MONITORING THE PRESENCE OR MOVEMENTS OF HUMANS

[75] Inventor: Martin J. Cohen, West Palm Beach, Fla.

[73] Assignee: Franklin GNO Corporation, West Palm Beach, Fla.

[21] Appl. No.: 839,775

[22] Filed: Jun. 18, 1969

[51] Int. Cl.² ............................................. G01N 37/08
[52] U.S. Cl. ......................................... 73/23; 324/459
[58] Field of Search .................. 73/23, 23.1; 340/237, 340/258 D, 276; 250/41.9 TF, 43.5; 324/33

[56] References Cited

U.S. PATENT DOCUMENTS

| | | | |
|---|---|---|---|
| 3,211,996 | 10/1965 | Fox et al. | 250/41.9 TF |
| 3,358,140 | 12/1967 | Curran et al. | 250/43.5 |
| 3,430,482 | 3/1969 | Draunieks et al. | 73/23.1 |

Primary Examiner—Verlin R. Pendegrass
Attorney, Agent, or Firm—Raphael Semmes

[57] ABSTRACT

Methods in which humans or other mobile bodies are exposed to volatile tracking and marking substances, the vapors of which are detected by ionizing gaseous samples, analyzing the ions in a drift field, and detecting at least a portion of the ions.

9 Claims, 1 Drawing Figure

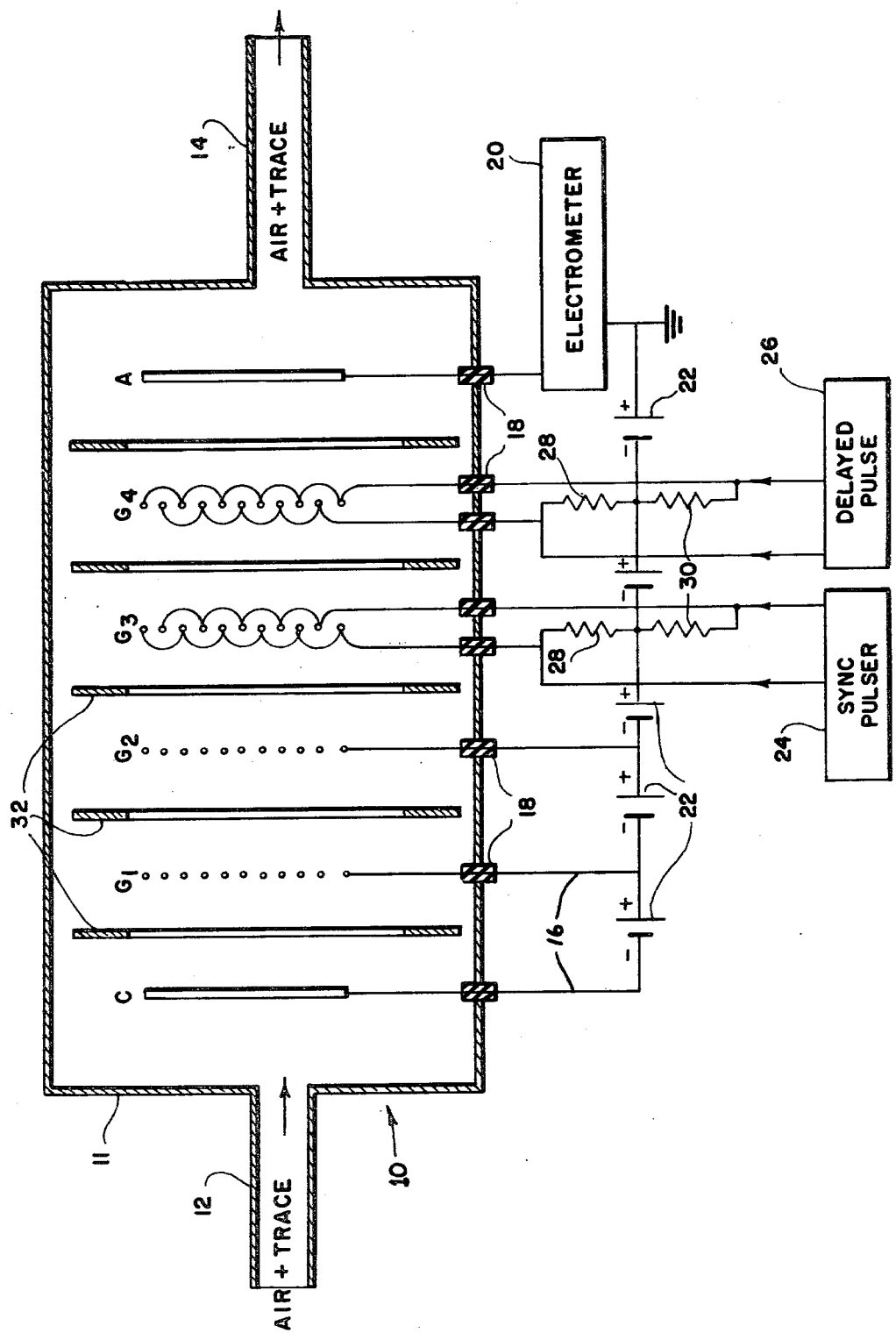

METHODS OF MONITORING THE PRESENCE OR MOVEMENTS OF HUMANS

BACKGROUND OF THE INVENTION

This invention relates to methods of monitoring the presence or movements of humans or other mobile bodies and is more particularly concerned with detecting the presence of humans in certain regions or the recent occupancy of such regions by humans.

In investigative operations, it is sometimes highly desirable to detect or confirm the presence of humans in particular regions, where they may be hidden from view, or to detect the recent occupancy of such regions by humans or other bodies. The ability to make determinations of this type is, inter alia, dependent upon the sensitivity of the measuring instruments with respect to the parameters, such as gaseous emissions, to be determined. The copending application of Martin J. Cohen, David I. Carroll, Roger F. Wernlund, and Wallace D. Kilpatrick, Ser. No. 777,964, filed Oct. 23, 1968, now U.S. Pat. No. 3,699,333 and entitled "Apparatus and Methods for Separating, Concentrating, Detecting, and Measuring Trace Gases", is capable of detecting trace gases at sensitivity of the order of one part in $10^{12}$. Succinctly stated, the system of that application involves the formation of primary ions and the reaction of the primary ions with molecules of trace substances to form secondary ions, which may be concentrated, separated, detected, and measured by virtue of the velocity or mobility of the ions in an electric field. A significant advantage of the system is that measurements are preferably performed at or about atmospheric pressure. The present invention is concerned with the utilization of the "Plasma Chromatography" technique of the said copending application in the monitoring of mobile bodies, by detecting substances to which the bodies have been intentionally exposed.

BRIEF DESCRIPTION OF THE INVENTION

It is accordingly a principal object of the invention to provide novel methods of monitoring mobile bodies and particularly the presence or movements of human bodies.

A further object of the invention is to provide novel methods of the foregoing type utilizing particular kinds of tracking and marking substances.

Briefly stated, in accordance with the present invention, ions are produced from collected gaseous samples of substances associated with mobile bodies, preferably human bodies, are analyzed in accordance with their velocity in a drift field, and are detected. The bodies are intentionally exposed to tracking and/or marking substances which produce ionizable vapors.

BRIEF DESCRIPTION OF THE DRAWING

The invention will be described hereinafter in conjunction with the accompanying drawing, which illustrates an exemplary apparatus which may be employed in the methods of the invention.

DETAILED DESCRIPTION OF THE INVENTION

In accordance with the invention, substances associated with human bodies are detected by Plasma Chromatography techniques involving ion production and analysis in a drift field. The present invention is particularly concerned with the intentional exposure of the bodies to tracking and/or marking substances which are volatile and produce ionizable vapors which can be detected by the Plasma Chromatography techniques. Marking involves attaching to the body a substance which produces vapor that can be detected directly from the body, while tracking involves attaching to the body a substance which leaves a volatile track or residue as the body moves about from place to place. The identifying substances may be strewn about on the ground, for example, in areas in which it is suspected the bodies to be detected will move. For example, such substances may be placed along a frontier through which the bodies to be detected may move or may be placed upon objects with which the bodies to be detected may come in contact. At some time thereafter, an area which may be adjacent to or remote from the original marking area will be monitored, and the presence of bodies in the monitored area or the recent occupancy of that area may be detected.

In accordance with the invention, it is preferred that the tracking and/or marking substance be a material which is uncommon in the environment, has a sufficiently low vapor pressure to produce persistence but still yield sufficient gaseous trace to be detectable by Plasma Chromatography measurements, and which is not readily detectable except by such measurements. Preferably, the substance is a non-toxic material, odorless or of unobtrusive odor, which clings to the body and yields a characteristic signal at a distance. Such substances, which may be liquid organic chemicals capable of clinging to or being absorbed by leather or rubber, will be referred to more fully hereinafter, but first the Plasma Chromatography technique will be described in conjunction with a representative instrument shown in the drawing.

Broadly, the Plasma Chromatography technique set forth in the aforesaid copending application involves the production of primary ions by subjecting the molecules of a suitable host gas, such as air, to ionizing radiation, for example. The primary ions are subjected to an electric drift field, causing them to migrate in a predetermined direction through a reaction space into which the sample or trace gas is introduced. The resultant collisions between the primary ions and the trace gas molecules produce secondary ions of the trace gas in much greater numbers than can be produced by mere electron attachment, for example, to the trace gas molecules. The secondary ions are also subjected to the electric drift field and may be sorted in accordance with their velocity or mobility. The specific system of the copending application employs a pair of successively arranged ion shutter grids or gates for segregating the ion species in accordance with their drift time. The opening of the first gate is timed to pass a group of ions, which may comprise unreacted primary ions as well as secondary or product ions, and the opening of the second gate is timed to pass a portion of the group to an ion detection means.

In the Plasma Chromatography apparatus illustrated in the drawing, which corresponds to apparatus shown and described in the aforesaid copending application, a drift cell 10 comprises an envelope 11, of metal, for example, having an inlet 12 and an outlet 14, which may constitute portions of a duct into which the envelope may be integrated. The envelope contains a series of electrodes, which may have parallel plane geometry, for example, and which may include a pair of principal electrodes C and A, a first passive grid G1, a second passive grid G2, a first shutter grid or ion gate G3, and a second shutter grid or ion gate G4. If the apparatus is to be employed to detect negative ions, electrode C will be a cathode and electrode A an anode, while if positive ions are to be detected, the polarities will be reversed. The electrodes may be spaced apart distances of the order of a few centimeters or less (e.g., cathode to anode spacing of about 10 centimeters) and may have lead wires 16 which pass through the envelope by means of insulators 18. The cathode or the region of the envelope near the cathode is provided with an ionizing means, such as a photoemission source, a radioactive source (e.g., tritium located at or near the cathode), a multiple point or wire array (corona) source, or an RF ionization source. The grids may be of the parallel wire type. Alternate wires of each of the shutter grids are connected together to form two separate groups, so that each shutter grid comprises two interdigitated sub-grids of parallel wires, each group of wires being provided with its own lead 16. The anode A may be a collector plate connected to an output device, such as the electrometer 20, which may be Cary Instruments Model 401 (vibrating reed) type with current sensitivity of $10^{-15}$ amps. at a time constant of 300 milliseconds.

An electric drift field is provided between the cathode, at a first region of the envelope 11, and the anode, at a second region of the envelope. In the form shown, the source of drift field is a series battery chain 22 with suitable taps being connected to the electrodes. Alternative sources of drift field, such as a resistive voltage divider with its ends connected to a DC supply, may be employed instead of the batteries. The anode A is connected to ground through the input circuit of the electrometer.

Adjacent elements of each shutter grid are normally maintained at equal and opposite potentials relative to a grid average potential established by the battery chain 22, and under these conditions, the shutter or gate is closed to the passage of electrically charged particles. The potential sources which provide the equal and opposite potentials just referred to may be considered to be part of grid drive circuits within blocks 24 and 26 entitled "Sync Pulser" and "Delayed Pulse". The components of these blocks are effective to drive the adjacent elements of each shutter grid to the same potential, the grid average potential, at predetermined instants, alternate grid wires being shown connected to the battery chain by resistors 28 and 30. The grids per se and circuits for driving the same are known in the art and need no further elucidation.

A series of guard rings 32 is provided along the perimeter of the envelope to maintain the uniformity of the electric field between the electrodes. The guard rings are also connected to successive points on the battery chain. Suitable supports and spacers, such as quartz rods and tubes, may be employed to support the various electrodes within the envelope.

The apparatus shown may be employed for detecting and measuring trace vapors which undergo ion-molecule reactions. The concentration of the trace vapors within a carrier gas, such a air, may be as little as one part in $10^{12}$ or even $10^{16}$. The apparatus can operate at pressures from as low as 5 torr to atmospheric and above as long as the gas collision mean free path is very much smaller than the cell dimensions.

In an illustrative use of the apparatus, air carrying a suitable gaseous trace substance, examples of which will be given hereinafter, flows through the envelope by means of the inlet 12 and the outlet 14. Any suitable source of flow pressure, such as a fan, may be employed to move the carrier gas and the trace substance. In the region between the cathode C and the first grid G1, primary ions of the carrier, or one or more of the main constituents thereof, such as oxygen, are formed under the influence of the ionizing means in this region. For example, low energy electrons may be provided at the cathode by a source of ultraviolet light (not shown) directed upon a reflective porous surface thereof, and negative oxygen ions may be formed at the cathode, as by direct attachment of the electrons to the oxygen molecules. The ions drift toward the anode A under the influence of the drift field.

The region from G1 to G2 is the ion-molecule reaction region. Within this region (and, of course, to a certain extent elsewhere within the envelope), the primary ions formed at the cathode react with molecules of the trace vapor to convert these molecules to secondary ions. In the region from C to G1, the electrons attach preferentially to the plentiful oxygen molecules, but in the region from G1 to G2, the oxygen reaction cross-section is sufficient to ensure a substantial and efficient conversion of trace vapor molecules to secondary ions.

The region from G2 to G3 is a potential isolation region for isolating the shutter grid G3 from the preceding regions of the envelope. During operation of the apparatus, shutter grid G3 is periodically opened to sample the products of the reaction and other ion species present. The opening of grid G3 at a predetermined time and for a predetermined duration constitutes a timed reference pulse during which a group of ions is passed into the ion mobility analysis region between G3 and G4. As the ions drift from G3 to G4, they become grouped or classified in accordance with their velocity (a function of mass) in the drift field. At a predetermined time delayed relative to the opening of grid G3, grid G4 is opened for a predetermined duration to select a portion of the ion mobility spectrum within the region G3 to G4 for passage to the anode. The ions which reach the anode produce a current in the electrometer 20, which may integrate the ion current over multiple cycles of cell operation. By scanning the time of opening of G4 relative to that of G3, a complete drift spectrum may be obtained in the output and recorded as a function of time, peaks in the output curve representing the response to detected ion species.

It is desirable, in general, to have the potential between C and G1 as high as convenient in order to reduce primary ion loss by processes of ion recombination and diffusion. In the ion-molecule reaction region from G1 to G2, however, it is desirable to have as long a time as possible to permit the desirable ion-molecule reaction to proceed to or toward completion, in order to give a definitive product mobility. Thus, the difference of potential between G1 and G2 is preferably low (e.g., 1 volt per centimeter), while the voltage gradient in the regions between C and G1 and between G2 and A is preferably substantially greater. Further details of the apparatus and its operation may be found in the aforesaid copending application.

The apparatus may readily be made portable (being provided with a portable power supply) and thus may be carried to a region which it is desired to monitor. Gaseous samples at the region may be taken continuously and analyzed at atmospheric pressure. The effects of moisture in the sample may be minimized by employing the inventions set forth in the copending application Ser. No. 779,096, filed Nov. 26, 1968 by Martin J. Cohen, Roger F. Wernlund, and David I. Carroll, and entitled "Apparatus and Methods for Separating, Detecting, and Measuring Trace Gases in the Presence of Moisture", and the copending application Ser. No. 780,851, filed Dec. 3, 1968 by David I. Carroll, Martin J. Cohen, and Roger F. Wernlund, and entitled "Apparatus and Methods for Separating, Detecting, and Measuring Trace Gases with Enhanced Resolution".

It now remains to describe the substances, alluded to above, which may be employed in the invention. In general, such substances include, but are not limited to, multicarbon compounds of oxygen, nitrogen, sulfur and/or phosphorus and the like, more particularly, substances in the following classes:

Aliphatic and aromatic

- esters
- ethers
- ketones
- aldehydes
- amine
- alcohols
- Halocarbons
- Nitrocarbons
- Sulphocarbons
- Phosphocarbons The fluoroethers and alcohols, organic phosphites, organic nitrates, and organic sulfur compounds appear to be especially suitable. The substances given in the following Table are representative of substances having the desired characteristics in accordance with the invention:

TABLE I

| Name | Formula | Vendors |
| --- | --- | --- |
| Carbon Tetrachloride | $CCl_4$ | duPont, PPG |
| R-11 or Trichlorofluoromethane | $CCl_3F$ | duPont, Pennsalt, Union Carbide, Allied Chemical |
| Bromochloromethane | $CH_2ClBr$ | Dow Chemical |
| Trichloroethane | $C_2H_3Cl_3$ | PPG |
| R-113 or Trichlorotrifluoroethane | $C_2Cl_3F_3$ | duPont, Pennsalt |
| R-114B2 or 1,2-Dibromotetrafluoroethane | $C_2Br_2F_4$ | duPont |
| R-C318 or Octafluorocyclobutane | $C_4F_8$(Cyclic) | duPont |
| R-C51-12 or Perfluorodimethylcyclobutane | $C_6F_{12}$(Cyclic) | duPont |
| Freon E-1 or Fluorinated Ether | $C_5HF_{11}O$ | duPont |
| Freon E-2 or Fluorinated Ether | $C_8HF_{17}O_2$ | duPont |
| Monochlorobenzene | $C_6H_5Cl$ | Hooker, PPG |
| p-Xylene | $C_6H_4(CH_3)_2$ | Allied Chemical |
| Isopropyl Chloride | $C_3H_7Cl$ | Hooker |
| 2,2,4-Trimethylpentane or Isoctane | $C_8H_{18}$ | Phillips Petroleum |
| Dimethyl sulfoxide | $(CH_3)_2SO$ | Eastman Organic Chemicals |
| Triethyl phosphite | $(C_2H_5O)_3P$ | Eastman Organic Chemicals |
| Diethyl glycerol nitrate | $(C_2H_5)_2(C_3H_5)ONO_2$ | duPont Chemical |
| Mono nitro toluene | $NO_2C_6H_4CH_3$ | Eastman Organic Chemicals |

The liquid substances to be detected may be readily handled by the well known technique of microencapsulation, the vapors being released when the strategically placed microcapsules are crushed or dissolved. A gram of a substance having molecular weight of 100 has $6 \times 10^{21}$ molecules. With an instrument sensitivity of $10^{-10}$ parts, and a sample volume of 10 cm$^3$, and a sampling time of 1 second, the number of molecules necessary for detection is $2.7 \times 10^{11}$. With a chemical vapor pressure of $10^{-2}$ torr, there are $3.6 \times 10^{14}$ molecules/cm$^3$ in the saturated vapor. The rate of loss of material depends on the surface area and the thickness of the effective layer of saturated vapor that is removed. Assuming a thickness value of 0.1 cm, a 45 cm/sec. breeze, and a 1 cm$^2$ surface, it is estimated that 4.5 cm$^3$/sec. of saturated vapor leave the source. A gram of the substance will last about 50 days and yet yield the equivalent of $10^4$ cm/sec. with a concentration above threshold signal.

While a preferred embodiment of the invention has been shown and described, it will be apparent to those skilled in the art that changes can be made in this embodiment without departing from the principles and spirit of the invention, the scope of which is defined in the appended claims.

The invention claimed is:

1. A method of monitoring a mobile body, which comprises exposing said body, at a first location, to a source of an unobtrusive tracking or marking substance which clings to the body in minute amounts upon contact therewith and is capable of producing an ionizable gas, thereafter collecting a gaseous sample at a second location to which the substance is carried by the body, forming ions of said substance from said gaseous sample by ion-molecule reactions, applying a DC drift field to said ions, segregating said ions in said drift field into groups in accordance with their drift velocity, and detecting at least a portion of the segregated ions of said substance, said ion forming and segregating steps being performed at a region maintained at a pressure such that the gas collision mean free path is very small compared to the dimensions of said region.

2. A method in accordance with claim 1, in which said body is exposed to a substance which leaves a track recording the movements of said body.

3. A method in accordance with claim 1, in which said body is exposed to a liquid organic substance.

4. A method in accordance with claim 1, in which said body is exposed to a non-toxic, substantially odorless substance.

5. A method in accordance with claim 1, in which said body is exposed to a substance selected from the group consisting of fluoroethers and alcohols, organic phosphites, organic nitrates, and organic sulfur compounds.

6. A method in accordance with claim 1, in which said body is exposed to a substance selected from the group consisting of aliphatic and aromatic esters, ethers, ketones, aldehydes, amine, alcohols; halocarbons; nitrocarbons; sulphocarbons; and phosphocarbons.

7. A method in accordance with claim 1, in which said body is exposed to a substance selected from Table I herein.

8. A method in accordance with claim 1, in which said substance is a substance capable of being absorbed by leather or rubber.

9. A method in accordance with claim 1, in which said body is a human body.